United States Patent
Moreau

(10) Patent No.: US 7,109,166 B1
(45) Date of Patent: Sep. 19, 2006

(54) SUSTAINED RELEASE FORMULATION OF A PEPTIDE

(75) Inventor: Jacques-Pierre Moreau, Upton, MA (US)

(73) Assignee: Societe de Conseils de Recherches et d'Applications Scientifiques, SAS, Paris (FR)

( * ) Notice: Subject to any disclaimer, the term of this patent is extended or adjusted under 35 U.S.C. 154(b) by 490 days.

(21) Appl. No.: 10/048,856

(22) PCT Filed: Aug. 16, 2000

(86) PCT No.: PCT/US00/22464

§ 371 (c)(1),
(2), (4) Date: May 15, 2002

(87) PCT Pub. No.: WO01/12233

PCT Pub. Date: Feb. 22, 2001

Related U.S. Application Data

(60) Provisional application No. 60/149,649, filed on Aug. 18, 1999.

(51) Int. Cl.
| | |
|---|---|
| A61K 38/12 | (2006.01) |
| A61K 9/52 | (2006.01) |
| A61K 9/14 | (2006.01) |
| A61K 38/00 | (2006.01) |
| A61K 47/30 | (2006.01) |
| A61K 47/12 | (2006.01) |
| A61K 47/48 | (2006.01) |
| A61K 31/74 | (2006.01) |
| A61K 9/00 | (2006.01) |
| A61K 38/04 | (2006.01) |
| A61K 38/31 | (2006.01) |
| A61P 1/00 | (2006.01) |
| A61P 1/12 | (2006.01) |
| A61P 35/02 | (2006.01) |

(52) U.S. Cl. ............... 514/11; 424/457; 424/484; 424/486; 424/489; 514/2; 514/772.3; 514/773; 514/806; 514/867; 514/908; 514/951; 514/964; 525/54.1; 525/444; 525/450

(58) Field of Classification Search ............... 525/54.1, 525/444, 450; 514/2, 806, 11, 772.3, 773, 514/867, 908, 951, 964; 424/457, 484, 486, 424/489
See application file for complete search history.

(56) References Cited

U.S. PATENT DOCUMENTS

| 5,552,520 A | 9/1996 | Kim et al. | |
|---|---|---|---|
| 5,672,659 A * | 9/1997 | Shalaby et al. ............ | 525/54.1 |

FOREIGN PATENT DOCUMENTS

| RU | 2 133 252 | 7/1999 |
|---|---|---|
| WO | WO 94/15587 | 7/1994 |
| WO | 95/04752 | 2/1995 |
| WO | WO 97/39738 | 10/1997 |
| WO | WO 97/40085 | 10/1997 |
| WO | WO 00/09166 | 2/2000 |
| WO | WO 00/43435 | 7/2000 |
| WO | WO 01/12232 | 2/2002 |

* cited by examiner

*Primary Examiner*—John Pak
*Assistant Examiner*—Ernst Arnold
(74) *Attorney, Agent, or Firm*—Fish & Richardson; Brian R. Morrill; Alan F. Feeney

(57) ABSTRACT

This invention is directed to a sustained release composition comprised of Compound (A) having the formula $$HO(CH_2)_2-N\diagup\diagdown N-(CH_2)-CO-$$
$$-D\text{-Phe-c}[Cys\text{-Tyr-D-Trp-Lys-Abu-Cys}]\text{-Thr-NH}_2,$$

or a pharmaceutically acceptable salt thereof, and a copolymer comprised of poly-(l)-lactic-glycolic-tartaric acid wherein the amino group of Compound (A) is ionically bound to a carboxyl group of the copolymer and wherein further the composition may be made into a sustained release pharmaceutical composition with pharmaceutically acceptable carrier(s).

8 Claims, 1 Drawing Sheet

SUSTAINED RELEASE FORMULATION OF A PEPTIDE

This application is a 371 of PCT/US00/22464 filed on Aug. 16, 2000, which claims the benefit of 60/149,649 filed on Aug. 18, 1999.

BACKGROUND OF THE INVENTION

This invention pertains to a sustained release complex, Compound (I), which comprises Compound (A), having the formula

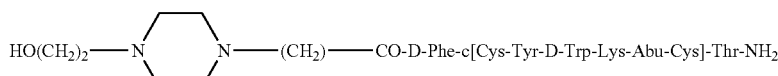

or a pharmaceutically acceptable salt thereof, and a copolymer comprising poly-(I)-lactic-glycolic-tartaric acid (P(I) LGT), wherein the amino group of said Compound (A) is ionically bound to a carboxyl group of the P(I)LGT. The present invention further pertains to a process for making said sustained release complex. Further still, the present invention is directed to a pharmaceutical composition comprising said sustained release complex and a pharmaceutically acceptable carrier(s).

Further, since Compound (A) is an analogue of somatostatin and it is well known to those skilled in the art that the known and potential uses of somatostatin are varied and multitudinous, this invention is also directed to the use of Compound (A), Compound (I) or microparticles of Compound (I) to treat a disease or condition in a patient in need thereof, which comprises administering Compound (A), Compound (I) or microparticles of Compound (I) to said patient, wherein the diseases or conditions to be treated are selected from the group consisting of gastroenterological conditions and/or diseases, such as Crohn's disease, systemic sclerosis, external and internal pancreatic pseudocysts and ascites, VIPoma, nesidoblastosis, hyperinsulinism, gastrinoma, Zollinger-Ellison Syndrome, diarrhea, AIDS related diarrhea, chemotherapy related diarrhea, scleroderma, Irritable Bowel Syndrome, pancreatitis, upper gastrointestinal bleeding, postprandial portal venous hypertension especially in cirrhotic patients, complications of portal hypertension, small bowel obstruction, gastroesophageal reflux, duodenogastric reflux and in treating endocrinological diseases and/or conditions, such as Cushing's Syndrome, gonadotropinoma, hyperparathyroidism, Graves' Disease, diabetic neuropathy, macular degeneration, hypercalcemia of malignancy, Paget's disease, and polycystic ovary disease; in treating various types of cancer such as thyroid cancer, leukemia, meningioma and conditions associated with cancer such as cancer cachexia; in the treatment of such conditions as hypotension such as orthostatic hypotension and postprandial hypotension and panic attacks.

Many drug delivery systems have been developed, tested and utilized for the controlled in vivo release of pharmaceutical compositions. For example, polyesters such as poly(DL-lactic acid), poly(glycolic acid), poly(ε-caprolactone) and various other copolymers have been used to release biologically active molecules such as progesterone; these have been in the form of microcapsules, films or rods (M. Chasin and R. Langer, editors, Biodegradable Polymers as Drug Delivery Systems, Dekker, NY 1990). Upon implantation of the polymer/therapeutic agent composition, for example, subcutaneously or intramuscularly, the therapeutic agent is released over a specific period of time. Such bio-compatible biodegradable polymeric systems are designed to permit the entrapped therapeutic agent to diffuse from the polymer matrix. Upon release of the therapeutic agent, the polymer is degraded in vivo, obviating surgical removal of the implant. Although the factors that contribute to polymer degradation are not well understood, it is believed that such degradation for polyesters may be regulated by the accessibility of ester linkages to non-enzymatic autocatalytic hydrolysis of the polymeric components.

Several EPO publications and U.S. Patents have addressed issues of polymer matrix design and its role in regulating the rate and extent of release of therapeutic agents in vivo.

For example, Deluca (EPO Publication 0 467 389 A2) describes a physical interaction between a hydrophobic biodegradable polymer and a protein or polypeptide. The composition formed was a mixture of a therapeutic agent and a hydrophobic polymer that sustained its diffusional release from the matrix after introduction into a subject.

Hutchinson (U.S. Pat. No. 4,767,628) controlled the release of a therapeutic agent by uniform dispersion in a polymeric device. It is disclosed that this formulation provides for controlled continuous release by the overlap of two phases: first, a diffusion-dependent leaching of the drug from the surface of the formulation; and second, releasing by aqueous channels induced by degradation of the polymer.

PCT publication WO 93/24150 discloses a sustained release formulation comprising a peptide having a basic group and a carboxy-terminated polyester.

U.S. Pat. No. 5,612,052 describes cation-exchanging microparticles made typically of carboxyl-bearing polyester chains onto which basic bioactive agents are immobilized to provide a control release system within an absorbable gel-forming liquid polyester.

Compound (A) is described and claimed in U.S. Pat. No. 5,552,520, which is assigned to the assignee hereof.

PCT publication WO 97/40085, assigned to the assignee hereof, discloses biodegradable polyesters comprising lactic acid units, glycolic acid units and hydroxy-polycarboxylic acid units such as tartaric acid or pamoic acid and processes for making said polyesters. More specifically, it discloses poly-lactide-glycolide-tartaric acid polymers in the ratio 65/33/2, respectively.

PCT publication WO 94/15587, assigned to the assignee hereof, discloses ionic conjugates of polyesters having free COOH groups with a bioactive peptide having at least one effective ionogenic amine. More specifically, it discloses that the polymers are made polycarboxylic by reacting the co-polymers with malic acid or citric acid. U.S. Pat. No. 5,672,659, is the U.S. national phase continuation application of WO 94/15587. U.S. Pat. No. 5,863,985 is a continuation of U.S. Pat. No. 5,672,659. Pending U.S. application Ser. No. 09/237,405 is a CIP of U.S. Pat. No. 5,863,985, which additionally discloses a polyester which must include citric acid, ε-caprolactone and glycolide; compositions comprising the immediately foregoing polyesters and a polypeptide; a polyester that must include tartaric acid as one of its members; compositions comprising the immediately foregoing polyester and a polypeptide; and the foregoing compositions in the shape of rods which are optionally coated with a biodegradable polymer.

PCT publication WO 97/39738, assigned to the assignee hereof, discloses a method of making microparticles of a sustained release ionic conjugate as described in WO 94/15587.

The contents of the foregoing patents, applications and publications are incorporated herein in their entirety.

The present invention is directed to a preferred embodiment of a sustained release ionic conjugate of polymer poly-lactide-glycolide-tartaric acid and Compound (A), also known as Compound (I), which is characterized by the surprising and non-obvious property of zero-order release of Compound (A) from the conjugate. More preferably, the ionic conjugate, Compound (I), is in the form of microparticles.

SUMMARY OF THE INVENTION

Figure 1:
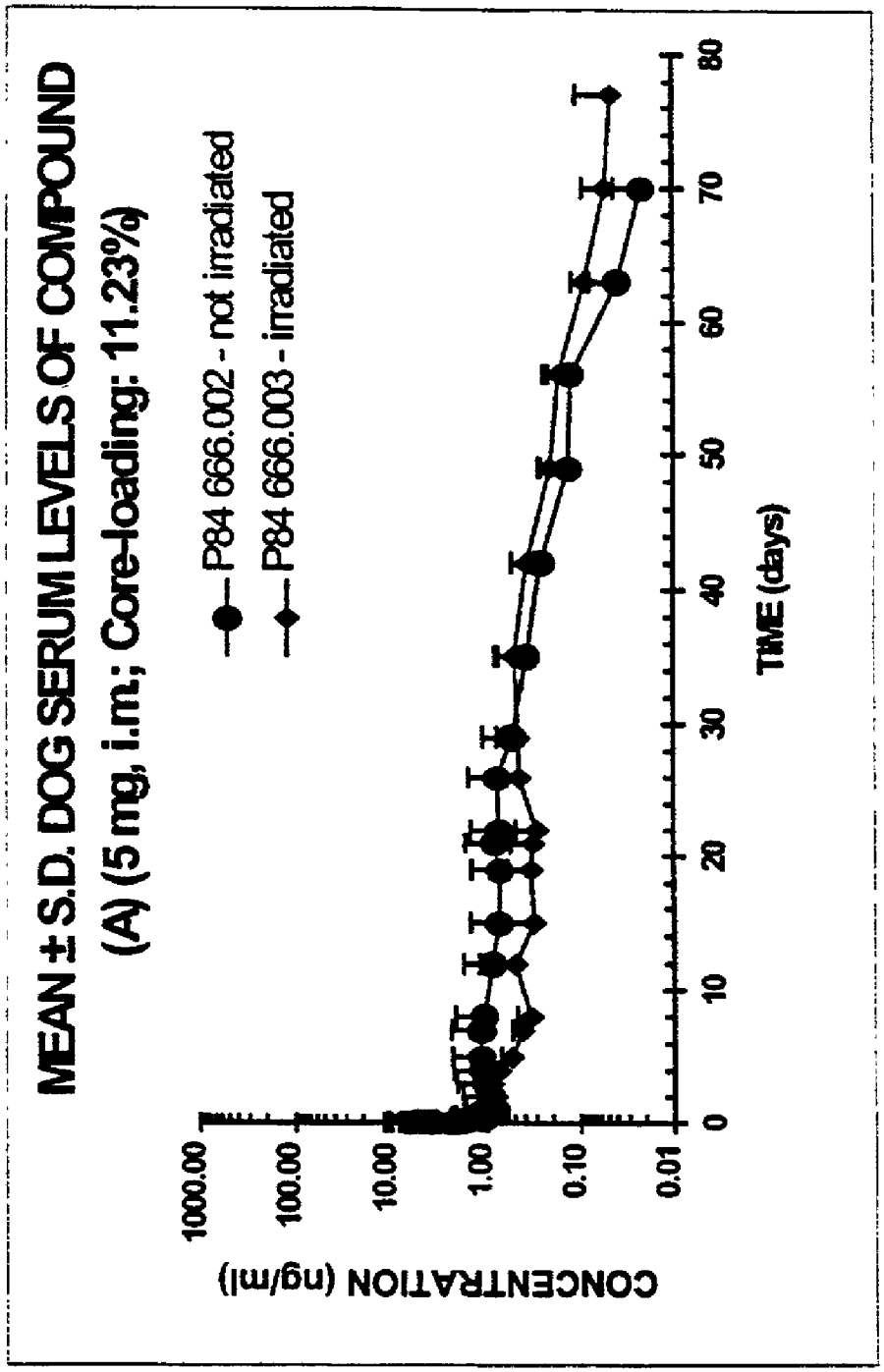
FIG. 1: Shows the in vivo release profile of Compound (A) from a sample of Compound (I) in dog, wherein the sample of Compound (I) consists of about 11.23% Compound (A), the polymer is I-lactide:glycolide:tartaric acid (72:27:1) and where Compound (I) is administered intramuscularly as microparticles. The irradiated sample refers to a sample of Compound (I) which was irradiated with γ-rays from a Cobalt source.

The present invention is directed to a Compound (I) which comprises Compound (A), having the formula

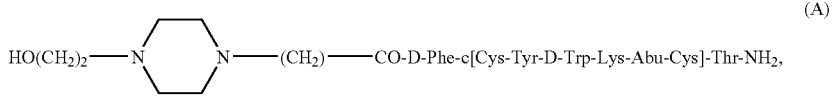

(A)

and a polymer, wherein the polymer comprises lactide units, glycolide units and tartaric acid units where the ratio in the polymer: of the lactide units is from and including about 71% to about 73%, of the glycolide units is from and including about 26% to about 28%; and of the tartaric acid units is from and including about 1% to about 3%; and where the amino group of Compound (A) is ionically bonded to a carboxylic group of the acid units of the polymer.

A preferred embodiment of Compound (I) is where the polymer consists of about 72% lactide units, about 27% glycolide units and about 1% tartaric acid units.

A preferred embodiment of the immediately foregoing Compound (I) is where the percentage of Compound (A) in Compound (I) is about 8% to about 12%.

In another aspect, the present invention is directed to microparticles of Compound (I) which comprises Compound (A), having the formula

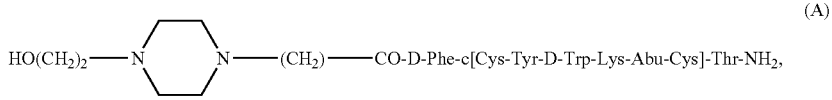

(A)

and a polymer, wherein the polymer comprises lactide units, glycolide units and tartaric acid units where the ratio in the polymer of the lactide units is from and including about 71% to about 73%, of the glycolide units is from and including about 26% to about 28%; and of the tartaric acid units is from and including about 1% to about 3%; and where the amino group of Compound (A) is ionically bonded to a carboxylic group of the acid units of the polymer.

Preferred microparticles of Compound (I), as described hereinabove, of this invention are those microparticles having a mean microparticle size of about 10 microns to about 100 microns.

More preferred microparticles of Compound (I), as described hereinabove, of this invention are those microparticles having a mean microparticle size of about 40 microns to about 70 microns.

Even more preferred microparticles of the present invention is where the microparticles exhibit a zero-order release profile of Compound (A) from the microparticles.

In yet another aspect, the present invention is directed to a pharmaceutical composition comprising microparticles comprising Compound (I) which comprises Compound (A), having the formula:

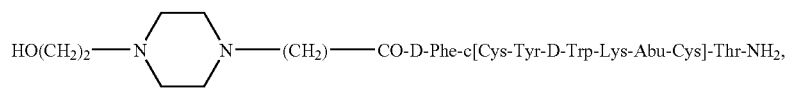

(A)

and a polymer, wherein the polymer comprises lactide units, glycolide units and tartaric acid units where the ratio in the polymer: of the lactide units is from and including about 71% to about 73%, of the glycolide units is from and including about 26% to about 28%; and of the tartaric acid units is from and including about 1% to about 3%; and where the amino group of Compound (A) is ionically bonded to a carboxylic group of the acid units of the polymer;

and optionally a pharmaceutically acceptable carrier, diluent or adjuvant.

In a further aspect, the present invention is directed to a method of treating a disease or condition in a patient in need thereof, which comprises administering to said patient an effective amount of Compound (A), as described hereinabove, or a pharmaceutically acceptable salt thereof, wherein the disease or condition is selected from the group consisting of systemic sclerosis, pancreatic pseudocysts, pancreatic ascites, VIPoma, nesidoblastosis, hyperinsulinism, gastrinoma, Zollinger-Ellison Syndrome, hypersecretory diarrhea, scleroderma, irritable bowel syndrome, upper gastrointestinal bleeding, postprandial portal venous hypertension, complications of portal hypertension, small bowel obstruction, duodenogastric reflux, Cushing's Syndrome, gonadotropinoma, hyperparathyroidism, diabetic neuropathy, macular degeneration, hypercalcemia of malignancy, Paget's disease, meningioma, cancer cachexia, psoriasis, hypotension and panic attacks.

In an even further aspect, the present invention is directed to a method of treating a disease or condition in a patient in need thereof, which comprises administering to said patient an effective amount of Compound (I), as described hereinabove, wherein the disease or condition is selected from the group consisting of systemic sclerosis, pancreatic pseudocysts, pancreatic ascites, VIPoma, nesidoblastosis, hyperinsulinism, gastrinoma, Zollinger-Ellison Syndrome, hypersecretory diarrhea, scleroderma, irritable bowel syndrome, upper gastrointestinal bleeding, postprandial portal venous hypertension, complications of portal hypertension, small bowel obstruction, duodenogastric reflux, Cushing's Syndrome, gonadotropinoma, hyperparathyroidism, diabetic neuropathy, macular degeneration, hypercalcemia of malignancy, Paget's disease, meningioma, cancer cachexia, psoriasis, hypotension and panic attacks.

In still a further aspect, the present invention is directed to a method of treating a disease or condition in a patient in need thereof, which comprises administering to said patient an effective amount of microparticles of Compound (I), as described hereinabove, wherein the disease or condition is selected from the group consisting of systemic sclerosis, pancreatic pseudocysts, pancreatic ascites, VIPoma, nesidoblastosis, hyperinsulinism, gastrinoma, Zollinger-Ellison Syndrome, hypersecretory diarrhea, scleroderma, irritable bowel syndrome, upper gastrointestinal bleeding, postprandial portal venous hypertension, complications of portal hypertension, small bowel obstruction, duodenogastric reflux, Cushing's Syndrome, gonadotropinoma, hyperparathyroidism, diabetic neuropathy, macular degeneration, hypercalcemia of malignancy, Paget's disease, meningioma, cancer cachexia, psoriasis, hypotension and panic attacks.

DETAILED DESCRIPTION

The term "about" as used herein in association with parameters and amounts, means that the parameter or amount is within ±5% of the stated parameter or amount.

The term "microparticle(s)" as used herein, refers to the micron size particles of the ionic conjugate comprising Compound (A) and poly-lactide-glycolide-tartaric acid polymer, which are preferably in essentially spherical form.

The instant application denotes amino acids using the standard three letter abbreviation known in the art, for example Phe=phenylalanine; Abu=α-aminobutyric acid.

As is well known to those skilled in the art, the known and potential uses of somatostatin are varied and multitudinous. Somatostatin is known to be useful in the treatment of the diseases and/or conditions listed hereinbelow. The varied uses of somatostatin may be summarized as follows: Cushings Syndrome (see Clark, R. V. et al, Clin. Res. 38, p. 943A, 1990); gonadotropinoma (see Ambrosi B., et al., Acta Endocr. (Copenh.) 122, 569–576, 1990); hyperparathyroidism (see Miller, D., et al., Canad. Med. Ass. J., Vol. 145, pp. 227–228, 1991); Paget's disease (see, Palmieri, G. M. A., et al., J. of Bone and Mineral Research, 7, (Suppl. 1), p. S240 (Abs. 591), 1992); VIPoma (see Koberstein, B., et al., Z. Gastroenterology, 28, 295–301, 1990 and Christensen, C., Acta Chir. Scand. 155, 541–543, 1989); nesidioblastosis and hyperinsulinism (see Laron, Z., Israel J. Med. Sci., 26, No. 1, 1–2, 1990, Wilson, D. C., Irish J. Med. Sci., 158, No. 1, 31–32, 1989 and Micic, D., et al., Digestion, 16, Suppl. 1.70. Abs. 193, 1990); gastrinoma (see Bauer, F. E., et al., Europ. J. Pharmacol., 183, 55 1990); Zollinger-Ellison Syndrome (see Mozell, E., et al., Surg. Gynec. Obstet., 170, 476–484, 1990); hypersecretory diarrhea related to AIDS and other conditions (due to AIDS, see Cello, J. P., et al., Gastroenterology, 98, No. 5, Part 2, Suppl., A163 1990; due to elevated gastrin-releasing peptide, see Alhindawi, R., et al., Can. J. Surg., 33, 139–142, 1990; secondary to intestinal graft vs. host disease, see Bianco J. A., et al., Transplantation, 49, 1194–1195, 1990; diarrhea associated with chemotherapy, see Petrelli, N., et al., Proc. Amer. Soc. Clin. Oncol., Vol. 10, P 138, Abstr. No. 417 1991); irritable bowel syndrome (see O'Donnell, L. J. D., et al., Aliment. Pharmacol. Therap., Vol. 4., 177–181, 1990); pancreatitis (see Tulassay, Z., et al., Gastroenterology, 98, No. 5, Part 2, Suppl., A238, 1990); Crohn's Disease (see Fedorak, R. N., et al., Can. J. Gastroenterology, 3, No. 2, 53–57, 1989); systemic sclerosis (see Soudah, H., et al., Gastroenterology, 98, No. 5, Part 2, Suppl., A129, 1990); thyroid cancer (see Modigliani, E., et al., Ann. Endocr. (Paris), 50, 483–488, 1989); psoriasis (see Camisa, C., et al., Cleveland Clinic J. Med., 57, No. 1, 71–76, 1990); hypotension (see Hoeldtke, R. D., et al., Arch. Phys. Med. Rehabil., 69, 895–898, 1988 and Kooner, J. S., et al., Brit. J. Clin. Pharmacol., 28, 735P–736P, 1989); panic attacks (see Abelson, J. L., et al., Clin. Psychopharmacol., 10, 128–132, 1990); sclerodoma (see Soudah, H., et al., Clin. Res., Vol. 39, p. 303A, 1991); small bowel obstruction (see Nott, D. M., et al., Brit. J. Surg., Vol. 77, p. A691, 1990); gastroesophageal reflux (see Branch, M. S., et al., Gastroenterology, Vol. 100, No. 5, Part 2 Suppl., p. A425, 1991); duodenogastric reflux (see Hasler, W., et al., Gastroenterology, Vol. 100, No. 5, Part 2, Suppl., p. A448, 1991); Graves' Disease (see Chang, T. C., et al., Brit. Med. J., 304, p. 158, 1992); polycystic ovary disease (see Prelevic, G. M., et al., Metabolism Clinical and Experimental, 41, Suppl. 2, pp 76–79, 1992); upper gastrointestinal bleeding (see Jenkins, S. A., et al., Gut., 33, pp. 404–407, 1992 and Arrigoni, A., et al., American Journal of Gastroenterology, 87, p. 1131, (abs. 275), 1992); pancreatic pseudocysts and ascites (see Hartley, J. E., et al., J. Roy. Soc. Med., 85, pp. 107–108, 1992); leukemia (see Santini, et al., 78, (Suppl. 1), p. 429A (Abs. 1708), 1991); meningioma (see Koper, J. W., et al., J. Clin. Endocr. Metab., 74, pp. 543–547, 1992); and cancer cachexia (see Bartlett, D. L., et al., Surg. Forum., 42, pp. 14–16, 1991). The contents of the foregoing references are incorporated herein by reference.

Applicant has now discovered that Compound (A), which is a somatostatin agonist, Compound (I) and microparticles of Compound (I), are particularly useful in treating the conditions, disorders and diseases noted hereinabove.

General Procedures:

Co-Polymer formation: The copolymer consisting of L-lactide, glycolide and L(+)-tartaric acid can be made according to methods well-known to those skilled in the art and as enabled herein. Accordingly, a reactor is loaded with monomers of glycolide, L-lactide and L(+)-tartaric acid and stannous 2-ethyl hexanoate in toluene solution. Preferably the molar percentages of L-lactide, glycolide, and L(+)-tartaric acid is about 72/27/1, respectively.

The L(+)-tartaric acid is previously dried, preferably over silica gel in an Abderhalden drying apparatus for about 10 hours. The reactor is then put under vacuum with stirring to remove toluene. The reactor, under an atmosphere of oxygen-free nitrogen, is then heated, preferably by immersing it in an oil bath, temperature=about 180° C. to 190° C., and stirring is increased to about 125 rpm. Prior to immersion, a heating tape is placed on the reactor lid. The time taken to completely melt the reactor contents is noted, typically about 15 minutes for a load of about 300 g at about 180° C. Samples are taken every hour during synthesis and analyzed by GPC to determine the percentage residual monomer and to obtain values for average molecular weight by number (Mn) and by weight (Mw) distributions. Typical reaction times are of the order of about 9 to 15 hours. The final polymer is also analyzed by titration to determine an acid number in meq/g and by GC to determine residual unreacted monomer content. Further analyses include IR (detection of characteristic C=O peak); NMR (determination of lactide and glycolide content in polymer) and residual tin (determination of residual tin due to use of stannous 2-ethyl hexanoate as catalyst).

Purification/Sodium salt formation of the above copolymer: Residual monomer (typically <5% (W/W)) is removed and the copolymer is converted to it's sodium salt form (to promote ionic salt formation) in one step. The poly-L-lactic-co-glycolic-co-L(+)-tartaric acid copolymer (PLGTA) is dissolved in acetone by sonication in a sonication bath to give a solution with a concentration in the range of 19–21% PLGTA by weight.

To this solution is added a weak solution of an inorganic base such as NaOH or $Na_2CO_3$, preferably 0.2M sodium carbonate—$Na_2CO_3$ is used, in an amount so that the resulting concentration of sodium is 1 to 2 times molar excess, preferably 1.2 times molar excess, over copolymer carboxyl groups. The solution is left to stir for about 15 to 60 minutes, preferably 30 minutes, at room temp. to aid sodium salt formation. It is then fed at about 50 to 300 ml/min, preferably about 100 ml/min, into a jacketed reactor containing de-ionized water cooled to about 1 to 4° C., preferably 2.5° C., using a circulation bath; the amount of water is about 20 to 30 times volumetric excess over acetone, preferably 20:1 volumetric excess over acetone. The water is stirred at a rate sufficient to create surface turbulence in order to avoid polymer agglomeration during precipitation using a paddle linked to a stirrer motor.

Once precipitation is complete, the dispersion is left to stir for a further 30 to 60 minutes to aid monomer removal before being placed in centrifuge bottles and spun. The supernatant is discarded and the cakes are resuspended in further de-ionized water, re-spun and dried, preferably by lyophilization.

Preparation of a Compound (A) Polymer Ionic Conjugate: The synthesis entails binding Compound (A) to the copolymer sodium salt in a medium in which both are soluble, preferably 3:1 (W/W) acetonitrile:water, followed by precipitation of the resulting ionic conjugate in de-ionized water and recovery of the water-insoluble conjugate precipitate formed.

A solution of the acetate salt of Compound (A) in de-ionized water is added to a solution consisting of a washed Na salt of 12,000 MW 71/28/1 to 73/26/1 PLGTA in acetonitrile (Range 24–26% (W/W) solution) to which a weak base such as 0.5M $Na_2CO_3$ has been added so that it results in about a 1.05 molar excess of Na over the acetate content of the Compound (A) acetate salt, and left to stir for about 5 minutes to provide an alkaline environment, preferably pH 8, to neutralize Compound (A)'s acetate group. Approximate weight ratio of acetonitrile:water=3:1. Based on target loading required (usually about 8% to about 12%), the quantity of Compound (A) required is determined. From this the volume of aqueous sodium carbonate required to neutralize the acetate of Compound (A) is determined and finally the volume of water for Compound (A) dissolution is calculated based on a desired final acetonitrile:water (including sodium carbonate added) volumetric ratio of about 3:1.

The Compound (A)-copolymer solution is left to stir for about 10 to 15 mins. at about 0 to 5° C., preferably 2.5° C., to facilitate ionic binding and discourage covalent binding (by use of low temperature) between the two components. The solution is then fed at a rate of about 50 to 300 ml/min into about a 20–30 to 1 volumetric excess of de-ionized water over the volume of acetonitrile in the foregoing 3:1 acetonitrile-water solution, stirred at a rate sufficient to provide surface agitation and avoid agglomeration and cooled to about 1 to 4° C., preferably 1.7° C., in a jacketed reactor connected to a circulation bath.

When precipitation is complete the dispersion is left to stir for a further 30 to 60 minutes to aid removal of water-soluble Compound (A)-oligomer compounds (oligomers are those lower molecular weight fractions of PLGTA, which are undesirable since they are water soluble) before being placed in centrifuge bottles and spun at about 5000 rpm for about 15 minutes in a centrifuge. The resultant centrifuge cakes are resuspended in de-ionized water and re-spun. They are then frozen and dried by lyophilization for 2 days and Compound (I) (Compound (A) ionically bound to PLGTA) is recovered. The loading is determined by HPLC analysis of the supernatant for unbound Compound (A) and nitrogen analysis (the Compound (A) nitrogen content is known and the polymer contains no nitrogen whatsoever). Extraction of Compound (A) from Compound (I) followed by HPLC analysis also allows determination of loading.

Compound (I) Nebulization: In order to provide a formulation well-suited for injection into a patient, Compound (I) is formulated into microspheres by dissolving it in ethyl acetate and using ultrasonic atomization (a.k.a. nebulization) to spray the solution into cold temperature, about −60° C. to −78° C., ethanol, isopropanol or a mixture of hexane and isopropanol, preferably isopropanol, which results in the formation of microspheres of Compound (I) upon contact with the cold isopropanol. The Compound (I) ethyl acetate solution can be sterilized by passing it through a 0.2 μm filter.

Compound (I) is dissolved in ethyl acetate preferably by sonication/stirring to give about 8% to about 12% (W/W) solution, preferably 12%, depending on polymer molecular weight and Compound (A) loading, both of which may after solution viscosity. This is fed at about 4.90 ml/min. to 5.10 ml/min., preferably 5.00 ml/min. to an industrial atomizer or nebulizer (Power—about 70%, Amplitude—about 80%, Frequency—about 34 to 35 kHz, preferably 34.50 kHz; in general the nebulizer should be powerful enough to generate a frequency which can uniformly spray (without "spitting") the Compound (I) ethyl acetate solution from about 8% to about 12% (W/W) in concentration, such concentrations lead to the formation of solid microspheres and the frequency should be such that a mean particle size of between 40 microns and 70 microns is obtained, which will allow ease of injection through a 21-gauge or a 19-gauge needle) and nebulized into a volume of isopropanol (IPA) that is 20 to 30 times, preferably 20 times, volumetric excess compared to the ethyl acetate volume, cooled to about −60° C. to about −78° C., cooling can be achieved, (e.g., via a reactor jacket, addition of dry ice or insertion of a cooling coil) and stirred at least at about 200 rpm (to avoid microsphere agglomeration). De-ionised water at a temperature of about 6° C. is fed at preferably 1.5 L/min to the nebulizer jacket to eliminate any local heating effects which can cause fouling of the nebulizer tip due to ethyl acetate evaporation. The solution nebulized evenly and an off-white particulate dispersion is seen to form in the IPA. This is allowed to thaw to about 0° C. to 22° C. over a period of about 30 mins. to 2 hrs before passing it through a 125 μm sieve (to remove any large non-injectable droplets/particles) and on to a Whatman no.1 filter paper where it is vacuum-filtered. The filter cake is rinsed with further IPA and then vacuum dried.

The present invention is illustrated by the following example but is not limited by the details thereof.

EXAMPLE 1

Ionic Conjugate of P(I)LGTA (72/27/1) and Compound A

Step A: Synthesis of 300 g of P(I)LG/Tartaric Acid Copolymer (I-lactide:glycolide:tartaric Acid=72:27:1)

A reactor was loaded with monomers of glycolide (Purac Biochem, Netherlands, 68.71 g), lactide (Purac Biochem, Netherlands, 227.53 g) and L(+)-Tartaric acid (Riedel-de Haen, Seelze, Germany, article number 33801, 3.75 g) and stannous 2-ethyl hexanoate (Sigma, St. Louis, Mo., USA, article number S-3252) in toluene (Riedel-de Haen, Seelze, Germany) solution (0.0982M, 4.47 ml). This corresponded to molar percentages of 71.81%; 26.82%; and 1.36% respectively of L-lactide, glycolide, and L(+)-tartaric acid.

The L(+)-tartaric acid was previously dried over silica gel (Riedel-de Haen, Seelze, Germany) in an Abderhalden drying apparatus for about 10 hours. The reactor (connected to a pump via a liquid nitrogen trap) was then put under vacuum (0.04 mbar) with stirring for about 50 minutes to remove toluene. The reactor, under an atmosphere of oxygen-free nitrogen (BOC gases, Dublin, Ireland, moisture content of 8 VPM), was then immersed in an oil bath (Temperature=~180° C.) and stirring was increased to 125 rpm. Prior to immersion, a heating tape (Thermolyne type 45500, input control setting=4) was placed on the reactor lid. The time taken to completely melt the reactor contents was noted, typically about 15 minutes for a load of 300 g at about 180° C. Samples were taken every hour during synthesis and analyzed by GPC to determine the percentage residual monomer and to obtain values for average molecular weight by number (Mn) and by weight (Mw) distributions. Typical reaction times were of the order of about 15 hours. The final polymer was also analyzed by titration to determine an acid number in meq/g and by GC to determine residual unreacted monomer content. Further analyses include IR (detection of characteristic C═O peak); NMR (determination of lactide and glycolide content in polymer) and residual tin (determination of residual tin due to use of stannous 2-ethyl hexanoate as catalyst).

Step B: Purification/Sodium Salt Formation with the Above Copolymer

Residual monomer (typically <5% (W/W)) was removed and the copolymer was converted to it's sodium salt form (to promote ionic salt formation) in one step. 81.05 g of a 12,000 g/mol 72/27/1 poly-L-lactic-co-glycolic-co-L(+)-tartaric acid copolymer (acid number by titration=0.231 meq/g) was dissolved in 324.24 g of acetone (Riedel-de Haen, Seelze, Germany) by sonication in a sonication bath (Branson, Danbury, Conn., USA) to give a solution with a concentration of 20.00% PLGTA by weight.

To this solution was added 56.17 ml of 0.2M $Na_2CO_3$ (Aldrich, Gillingham, Dorset, UK), thus providing a 1.2 times molar excess of sodium over copolymer carboxyl groups. The solution was left to stir for about 30 minutes at room temp. to aid sodium salt formation. It was then fed at ~100 ml/min into a 10 L jacketed reactor containing 8.2 L of de-ionized water (approximately a 20:1 volumetric excess over acetone cooled to about 2.5° C. using a circulation bath (Huber, Offenburg, Germany). This water was stirred at 800 rpm to create surface turbulence and avoid polymer agglomeration during precipitation using a paddle linked to a stirrer motor.

Once precipitation was complete, the dispersion was left to stir for a further 30 mins. to aid monomer removal before being placed in centrifuge bottles and spun at 5000 rpm for about 15 minutes in a Sorvall centrifuge (DuPont Sorvall Products, Wilmington, Del., USA). The supernatant was discarded and the cakes were resuspended in further de-ionized water, respun and frozen in a freezer (−13° C.) overnight before being dried in a small-scale lyophilizer (Edwards, Crawley, West Sussex, UK) the next day. This lyophilizer contains no coolant system. After 5 days of lyophilization 65.37 g of washed copolymer were recovered representing a yield of 80.65%.

Step C: Preparation of Compound (I)

A solution of 1.27 g of the acetate salt of Compound (A) (Batch 97K-8501 from Kinerton Ltd., Dublin, Ireland, potency=85.8% (potency refers to the percent free base peptide present in the peptide acetate salt); acetate=10.87%) in 5.87 g of de-ionized water was added to a solution consisting of 8.01 g of a washed Na salt of 12,000 MW 72/27/1 PLGTA in 24.84 g acetonitrile (Riedel de-Haen) (24.38% (W/W) solution to which 2.41 ml of 0.5M $Na_2CO_3$ (this corresponds to a 1.05 excess of Na over the acetate content of Compound (A)-acetate salt) had been added and left to stir for about 5 minutes to provide an alkaline environment (pH 8) for neutralization of Compound (A)'s acetate groups. Approximate weight ratio of acetonitrile: water=3:1. Based on target loading required, the quantity of Compound (A) required was determined. From this the volume of aqueous sodium carbonate required to neutralize the acetate of Compound (A) was determined and finally the volume of water for Compound (A) dissolution was calculated based on a desired final acetonitrile:water (including sodium carbonate added) volumetric ratio of 3:1.

The Compound (A)-copolymer solution was left to stir for about 15 mins. at about 2.5° C. to facilitate ionic and discourage covalent binding between the two. The solution was then fed at ~100 ml/min into 630 ml (approximately a 20:1 volumetric excess over acetonitrile) of de-ionized water stirred at 350 rpm (to provide surface agitation and avoid Compound (A)-copolymer agglomeration) and cooled to about 1.7° C. in a 6 L jacketed reactor connected to a circulation bath.

When precipitation was complete the dispersion was left to stir for a further 30 minutes to aid removal of water-soluble Compound (A)-oligomer compounds before being placed in centrifuge bottles and spun at 5000 rpm for about 15 minutes in a Sorvall centrifuge (DuPont Sorvall Products, Wilmington, Del., USA). The resultant centrifuge cakes were resuspended in de-ionized water and re-spun. They were then frozen and dried by lyophilization for 2 days. 8.30 g of the title product were recovered representing a yield of 91.38%. The loading was determined by HPLC analysis of the supernatant for unbound Compound (A) and nitrogen analysis (the Compound (A) nitrogen content is known and the polymer contains no nitrogen whatsoever). Extraction of Compound (A) from Compound (I) followed by HPLC analysis also allows determination of loading, which for this example was 11.25%.

Step D: Compound (I) Nebulization 8.27 g of Compound (I) from step C was dissolved in 60.77 g of ethyl acetate by sonication/stirring (room temp.) to give a 12.00% (W/W) solution. This was fed at 5 ml/min to an industrial atomizer/nebulizer (Martin Walter Powersonic Model MW400GSIP, available from Sodeva, France), Power=70%, Amplitude=80%, Frequency=34.50 kHz and nebulized into 1.35 L of isopropyl alcohol (IPA) (20 times volumetric excess compared to ethyl acetate volume) cooled to about −74±4° C. (cooling achieved via reactor jacket) and stirred at 200 rpm (to avoid microsphere agglomeration) in a jacketed reactor. De-ionised water at a temperature of 6° C. was fed at 1.5 L/min to the nebulizer jacket to eliminate any local heating effects which can cause fouling of the nebulizer tip due to ethyl acetate evaporation. The solution nebulized evenly and an off-white particulate dispersion was seen to form in the IPA. This was allowed to thaw to about 0° C.–4° C. over a period of about 30 mins. to 2 hrs before passing it through a 125 μm sieve (to remove any large non-injectable droplets/particles) and on to a Whatman no. 1 filter paper where it was vacuum-filtered. The filter cake was rinsed with further IPA and then vacuum dried. 6.88 g of injectable material was obtained representing a yield of 83.19%. The microparticles of Compound (I) had a mean particle size of about 54 microns.

The in vivo release of Compound (A) from microparticles of Compound (I) can be and were tested according to the following description. The in vivo study was designed to evaluate the in vivo release profile of Compound (A) following the intramuscular administration of microparticles of Compound (I) to male Beagle dogs by means of the pharmacokinetic profile of Compound (A) following its administration.

Pharmaceutical formulations of microparticles of Compound (I) were administered intramuscularly in the rear leg muscles. Following a single intramuscular administration of the irradiated or non-irradiated prepared pharmaceutical forms containing microparticles of Compound (I) (amount of microparticles injected corresponded to 5 mg of Compound (A) based upon the determination that Compound (A) loading in Compound (I) was 11.23%) to groups of six dogs each per pharmaceutical form. The quantitation of Compound (A) in serum samples and the pharmacokinetic analysis is conducted as follows.

Blood collection from the dogs are carried out before injection (time 0), and 5, 15 and 30 min; 1, 2, 4, 8 and 12 hrs; 1, 2, 3 and 4 days; then twice per week over the first month (for example on Mondays and Thursdays); and finally once a week from the second month until completing the experiment, when the serum levels of Compound (A) were no longer detected. However, the real times of blood collection were recorded and used in the pharmacokinetic analysis. Blood samples (5 ml) at times 0 (before i.m. administration) and at 7, 21, 35, 56 and 84 days after the i.m. injection and blood samples (4 ml) for the rest of sampling times, were taken through the jugular or the cephalic veins at the prescribed times.

The samples were placed in two fractions: one about 2.5 ml or 3.5 ml in certain fixed time samplings, in tubes that contain 50 and 80 μl, respectively, of a solution of aprotinin (10 ml of Trasylol® 500000 KJU lypophillised and rediluted in 2 ml of p.p.i. water) and the other one about 1.5 ml in tubes that were allowed to stand.

After the red cells clot, the tubes were centrifuged for 20 min at 30000 r.p.m. at +4° C. Serum with aprotinin were removed and stored in two fractions at −20° C. until the sample was analyzed for Compound (A).

The concentration of Compound (A) in the serum samples were analyzed by a radioimmunoassay method. Standard curves with blank dog plasma and Compound (A) standard solutions were prepared daily. In this method the limit of quantification for Compound (A) in dog serum samples is about 0.050 nanograms (ng)/ml. The areas under the curve (AUC) and the maximum serum concentration ($C_{max}$) were normalized by the dose supplied (dose adminstered to each of the animals expressed in μg/kg). The index of the absorption rate ($C_{max}$/AUC) were also calculated.

The results of the foregoing experiment are shown in FIG. 1.

Compound (A) or a pharmaceutically-acceptable salt thereof, Compound (I) or microparticles of Compound (I) can be administered by oral, parenteral (e.g., intramuscular, intraperitoneal, intravenous or subcutaneous injection, or implant), nasal, vaginal, rectal, sublingual or topical routes of administration and can be formulated with pharmaceutically acceptable carriers to provide dosage forms appropriate for each route of administration.

Solid dosage forms for oral administration include capsules, tablets, pills, powders and granules. In such solid dosage forms, the active compound is admixed with at least one inert pharmaceutically acceptable carrier such as sucrose, lactose, or starch. Such dosage forms can also comprise, as is normal practice, additional substances other than such inert diluents, e.g., lubricating agents such as magnesium stearate. In the case of capsules, tablets and pills, the dosage forms may also comprise buffering agents. Tablets and pills can additionally be prepared with enteric coatings.

Liquid dosage forms for oral administration include pharmaceutically acceptable emulsions, solutions, suspensions, syrups, the elixirs containing inert diluents commonly used in the art, such as water. Besides such inert diluents, compositions can also include adjuvants, such as wetting agents, emulsifying and suspending agents, and sweetening, flavoring and perfuming agents.

Preparations for parenteral administration include sterile aqueous or non-aqueous solutions, suspensions, or emulsions. Examples of non-aqueous solvents or vehicles are propylene glycol, polyethylene glycol, vegetable oils, such as olive oil and corn oil, gelatin, and injectable organic esters such as ethyl oleate. Such dosage forms may also contain adjuvants such as preserving, wetting, emulsifying, and dispersing agents. They may be sterilized by, for example, filtration through a bacteria-retaining filter, by incorporating sterilizing agents into the compositions, by irradiating the compositions, or by heating the compositions. They can also be manufactured in the form of sterile solid compositions which can be dissolved in sterile water, or some other sterile injectable medium immediately before use.

Compositions for rectal or vaginal administration are preferably suppositories which may contain, in addition to the active substance, excipients such as coca buffer or a suppository wax.

Compositions for nasal or sublingual administration are also prepared with standard excipients well known in the art.

It is preferred that the microparticles of Compound (I) be administered via parenteral administration or oral administration.

The effective dosage of the microparticles of Compound (I) to be administered to a patient can be determined by the attending physician or veterinarian and will be dependent upon the proper dosages contemplated for Compound (A) and the loading of Compound (A) in the microparticles of Compound (I). Such dosages will either be known or can be determined by one of ordinary skill in the art. Preferably the dosage should result in a level of at least 200 picograms/ml of Compound (A) in the patient.

The use of immediate or of sustained release compositions depends on the type of indications aimed at. If the indication consists of an acute or over-acute disorder, a treatment with an immediate release form will be preferred over a prolonged release composition. On the contrary, for preventive or long-term treatments, a prolonged release composition will generally be preferred.

Typically, the indication of upper gastrointestinal bleeding will correspond an acute or over-acute treatment with a dosage of about 80 to 120 µg/day per person during approximately 5 days. After endoscopical treatment, preventive treatment against recurrence can be performed using microparticles of Compound (A) or other sustained release forms as an adjuvant to usual treatments.

For other indications other than upper gastrointestinal bleeding, which require rather long term treatments, microparticles of Compound (I) will be preferred.

The invention claimed is:

1. A composition comprising a complex comprised of Compound (A) having the formula

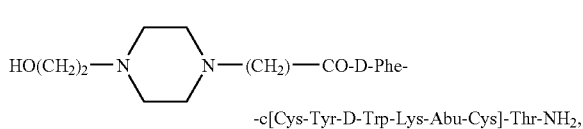

and a polymer wherein the polymer comprises 71% to 73% lactide units, 26% to 28% glycolide units and 1% to 3% tartaric acid units and the amino group of Compound (A) is ionically bonded to a carboxylic group of the acid units of the polymer.

2. A composition according to claim 1, wherein the polymer consists of 72% lactide units, 27% glycolide units and 1% tartaric acid units.

3. A composition according to claim 2, wherein the percentage of Compound (A) in the composition is about 8% to about 12%.

4. A composition according to claim 1, wherein said composition is in the form of microparticles.

5. Microparticles according to claim 4, wherein the mean microparticle size is about 10 microns to about 100 microns.

6. Microparticles according to claim 5, wherein the mean microparticle size is about 40 microns to about 70 microns.

7. Microparticles according to claim 6, wherein said microparticles exhibit a zero-order release profile of Compound (A).

8. A pharmaceutical composition comprising microparticles of claim 4 and a pharmaceutically acceptable carrier, diluent or adjuvant.

* * * * *